United States Patent
Wahlgren et al.

(10) Patent No.: US 9,402,999 B2
(45) Date of Patent: Aug. 2, 2016

(54) TRANSDERMAL MEDICAL PATCH

(75) Inventors: Stephen Wahlgren, Easton, PA (US); Martin J. Nohilly, Murray Hill, NJ (US); Anthony R. DiUbaldi, Jackson, NJ (US); Rex O. Bare, Preston, CT (US); Bradley Sargent, Mission Viejo, CA (US); Michael W. Ammerman, San Clemente, CA (US); Jeffrey C. Smith, Irvine, CA (US); Kathryn M. Kukulka, Laguna Beach, CA (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 565 days.

(21) Appl. No.: 13/464,634

(22) Filed: May 4, 2012

(65) Prior Publication Data

US 2013/0296996 A1  Nov. 7, 2013

(51) Int. Cl.
*A61N 1/04* (2006.01)
*A61N 1/30* (2006.01)
*A61N 1/36* (2006.01)

(52) U.S. Cl.
CPC .............. *A61N 1/303* (2013.01); *A61N 1/0428* (2013.01); *A61N 1/0456* (2013.01); *A61N 1/0492* (2013.01); *A61N 1/36014* (2013.01)

(58) Field of Classification Search
CPC .............. A61N 1/0492; A61N 1/0456; A61N 1/36014; A61N 1/0452; A61N 1/0428; A61N 1/046; A61N 1/0551; A61N 1/0468; A61N 1/0484; A61B 2562/125; A61B 5/04087; A61B 5/0408; A61B 5/6833; A61B 2560/0412
USPC ......................................................... 607/149
See application file for complete search history.

(56) References Cited

U.S. PATENT DOCUMENTS

| | | | | |
|---|---|---|---|---|
| 4,706,680 A | * | 11/1987 | Keusch et al. | 600/392 |
| 4,776,350 A | * | 10/1988 | Grossman et al. | 607/152 |
| 4,838,273 A | * | 6/1989 | Cartmell | 600/385 |
| 5,520,683 A | * | 5/1996 | Subramaniam et al. | 606/32 |
| 5,660,178 A | * | 8/1997 | Kantner et al. | 600/391 |
| 5,779,632 A | * | 7/1998 | Dietz et al. | 600/391 |
| 6,019,877 A | * | 2/2000 | Dupelle et al. | 204/196.11 |
| 6,445,955 B1 | * | 9/2002 | Michelson et al. | 607/46 |

(Continued)

FOREIGN PATENT DOCUMENTS

| WO | 91/15257 | 10/1991 |
|---|---|---|
| WO | 98/28038 | 7/1998 |
| WO | 02/074385 | 9/2002 |

OTHER PUBLICATIONS

International Search Report for counterpart application PCT/US2013/039288, mailed Jun. 20, 2014 (6 pages).

*Primary Examiner* — Christopher D Koharski
*Assistant Examiner* — Jeremiah Kimball
(74) *Attorney, Agent, or Firm* — Cohen & Hildebrand, PLLC

(57) ABSTRACT

A medical patch having a multi-piece bottom liner including a central liner sequentially removable independently of two outer perimeter liners. The multi-piece liner covering two adhesives of different peel force. Removal of the central liner exposes a first temporary/repositionable adhesive. Once properly positioned, the outer perimeter liners are removed to expose a second stronger adhesive. A foam cushioning layer is disposed beneath and extends beyond a footprint of every printed circuit board to prevent skin irritation. The medical patch may be designed specifically for stimulation of the sacral (S3 foramen) spinal nerve without the use of a separate mechanical placement tool or assistance by another.

7 Claims, 12 Drawing Sheets

(56) References Cited

U.S. PATENT DOCUMENTS

| | | |
|---|---|---|
| 8,126,530 B2 * | 2/2012 | Bare et al. .................. 600/397 |
| 2004/0088036 A1 * | 5/2004 | Gilbert ........................ 607/148 |
| 2005/0277998 A1 | 12/2005 | Tracey et al. |
| 2006/0195153 A1 | 8/2006 | DiUbaldi et al. |
| 2008/0215128 A1 * | 9/2008 | Rainey et al. ............... 607/152 |
| 2009/0132018 A1 | 5/2009 | DiUbaldi et al. |
| 2010/0076533 A1 * | 3/2010 | Dar et al. ................... 607/115 |
| 2010/0082079 A1 * | 4/2010 | Skahan et al. ............... 607/46 |
| 2010/0222734 A1 * | 9/2010 | Jayes et al. ................. 604/20 |
| 2011/0152987 A1 * | 6/2011 | Wahlgren et al. ........... 607/115 |
| 2011/0237922 A1 * | 9/2011 | Parker et al. ............... 600/382 |
| 2011/0245711 A1 * | 10/2011 | Katra et al. ................. 600/547 |
| 2011/0270360 A1 * | 11/2011 | Harris et al. ................ 607/62 |
| 2011/0288604 A1 * | 11/2011 | Kaib et al. .................. 607/5 |
| 2013/0110220 A1 * | 5/2013 | Brown ........................ 607/149 |

\* cited by examiner

TRANSDERMAL MEDICAL PATCH

BACKGROUND OF THE INVENTION

1. Field of the Invention

The present invention is directed to a medical patch and, in particular, an improved transdermal medical patch for providing a treatment therapy such as electrical stimulation and/or delivery of a pharmacological agent such as pain medication, drugs, and hormones.

2. Description of Related Art

Nerves are part of the peripheral nervous system of a human body. They convey sensory signals back and forth from the skin and body organs to the central nervous system. Nerves may become damaged due to wear and tear, physical injuries, infection, and/or the failure of the blood vessels surrounding the nerves. These functional defects may be accompanied by pain, numbness, weakness and in some cases, paralysis. Other problems resulting from damaged nerves may include urinary and fecal incontinence.

Different approaches have been developed to treat the above-mentioned problems. For example, treating urinary incontinence may involve behavior modification such as urinating more frequently and wearing protective undergarments. In certain social situations, however, individuals may not be able to follow the practice of frequent urination or wearing protective undergarments. Another approach involves a medical therapy including taking prescribed drugs. However, this methodology may result in adverse side effects or drug interactions that will ultimately require discontinuation.

Still another technique for treating the above-noted conditions involves stimulation using an electro-medical device that is positioned near a target nerve. One such electro-medical device is commonly referred to as an Implantable Pulse Generator (IPG), which typically includes one or more electrodes, an electrical pulse generator and a power source (e.g., internal and/or external to the body). The electrical pulse generator generates an electrical signal adapted to stimulate a target nerve. When the electrodes receive the signal from the generator, they draw energy from the power source and generate an electric field of suitable strength to stimulate the target nerve.

Implantable Pulse Generators are somewhat effective for stimulating nerves; however, such devices are extremely invasive since they are implanted inside a patient's body during a surgical procedure. Furthermore, IPG's consume a significant amount of power, which may be due to an increase in electrical impedance between the electrodes, or an increase in electrical impedance between the electrodes and the IPG. Increased power consumption may also be caused by a phenomenon referred to as "desensitization of stimulus," whereby the human body responds to an applied external charge by offering a resistance to the applied external charge. The body resists the applied external charge by increasing the stimulation threshold for a target nerve, thereby rendering the earlier stimulus level ineffective. To overcome this problem, a more powerful charge must be generated, which consumes even more battery power and requires frequent replacement and/or recharging of the batteries.

With some nerve stimulation devices, it has been observed that the generated electric field spreads widely, undesirably affecting untargeted muscles and nerves along with the target nerve. The wide spreading of the electric field significantly reduces the strength of the electrical signal at the target nerve. In order to properly stimulate the target nerve, the strength of the electrical signal must be substantially increased, which requires the device to draw more power from the battery thereby consuming greater energy.

In view of the aforementioned drawbacks, efforts have been sought to stimulate nerves in a more efficacious and non-invasive manner. For example, non-invasive selective nerve stimulation (SNS) medical patches are disclosed in commonly assigned U.S. Patent Publication Nos.: 2005/0277998, filed Jun. 7, 2005 and 2006/0195153, filed Jan. 31, 2006, the disclosures of which are each hereby incorporated by reference in their entirety herein. Specifically, in one or more embodiments thereof, these publications teach a non-invasive, transcutaneous neurostimulation patch that generates and transmits a controlled, amplitude-modulated waveform comprising a carrier signal and a pulse envelope. The carrier waveform is designed to be of sufficient frequency to overcome attenuation due to tissue impedances. The pulse envelope contains specific pulse width, amplitude and shape information designed to stimulate specific nerves.

Medical patches are often adhered to a patient's skin with an active or operating portion of the patch directed toward a target location (e.g., one or more targeted nerves) on the patient. Such medical patches are disclosed in commonly assigned U.S. Patent Publication Nos. 2009/0132018, filed on Nov. 16, 2007 and 2011/0152987, filed on Dec. 18, 2009, the disclosures of which are each hereby incorporated by reference in their entirety herein. The medical patch produces electrical signals and/or delivers a pharmacological agent for achieving a therapeutic benefit to a target site of the body. In some instances, a series of medical patches are sequentially in time applied to the patient, whereby a first medical patch applied by a medical professional is removed from a patient's skin and replaced with a second medical patch. After the passage of time, the second medical patch is removed and replaced by a third medical patch, and so on. Rather than being administered by a physician, nurse or technician, application of the second and subsequent medical patches to the body is often conducted by the patient himself/herself at home. Due to inexperience, replacement medical patches may be improperly aligned over the target site on the patient, e.g. a particular nerve that is the target for nerve stimulation, resulting in less effective treatment therapy. Thus, there is a need to develop a medical patch that may be properly positioned on the body by the patient himself/herself unassisted. The use a separate mechanical placement tool to properly position the medical patch on the body, although permitting self-placement, disadvantageously increases the overall cost and complexity of use while being susceptible to becoming lost or misplaced. All of these concerns may reduce usage of the medical patch thereby limiting the efficacy of treatment therapy.

Once again the lack of experience by the patient in self-positioning the medical patch on the body himself/herself increases the probability of its improper placement on the target site of the body. Such improper positioning of the medical patch may be readily observed visually once it has been adhered to the body. The occurrence of misplacement of the medical patch is particularly significant until the patient becomes more familiar with how to properly position the patch on the body over the target site. In anticipation of such learning curve by the patient, it would be desirable to temporarily adhere the medical patch to the body and visually confirm if it has been properly positioned at the target site. If not correctly located on the body, it would be advantageous to allow the medical patch to be removed and repositioned correctly on the body without having to use a new patch.

With the introduction of small electronic component circuitry today, transcutaneous medical patches typically include electronic circuitry that may, over time, cause skin irritation, redness or lesions. This is of particular concern when the same medical patch remains adhered at the same location on the body for an extended period of time, for example, several days or more. It would therefore be desirable to reduce the occurrence of skin irritation thereby increasing the duration of time over which the medical patch may remain adhered to the same location on the body.

In view of the foregoing, there is a need for medical patch that overcomes the aforementioned problems associated with convention transdermal patches.

SUMMARY OF THE INVENTION

The present invention is directed to an improved system and method for self-positioning and aligning medical patches that provide a treatment therapy in the form of electrical signals and/or pharmacological agents such as pain medication, drugs, and hormones. The medical patch in accordance with the present invention enables patients, while at home and unassisted, to self-locate and place medical patches over one or more target sites on the patient's body.

One aspect of the present invention is directed to a medical patch having a multi-piece bottom liner including a central liner sequentially removable independently of two outer perimeter liners. The multi-piece liner covering two adhesives of different peel force. Removal of the central liner exposes a first temporary/repositionable adhesive. Once properly positioned, the outer perimeter liners are removed to expose a second stronger adhesive. A foam cushioning layer is disposed beneath and extends beyond a footprint of every printed circuit board to prevent skin irritation. The medical patch may be designed specifically for stimulation of the sacral (S3 foramen) spinal nerve without the use of a separate mechanical placement tool or assistance by another.

Another aspect of the present invention is directed to a medical patch having an outer perimeter extending between a leading end and a trailing end. The medical patch has electronic circuitry including at least one printed circuit board; and a cushioning layer having a bottom surface, an opposite top surface, a side surface and an outer perimeter. The at least one printed circuit board is disposed on the top surface of the cushioning layer. The outer perimeter of the cushioning layer extends two dimensionally in all directions beyond a footprint of each of the at least one printed circuit board.

Yet another aspect of the present invention is directed to a medical patch having an outer perimeter extending between a leading end and a trailing end. The medical patch has electronic circuitry including at least one printed circuit board; and a cushioning layer having a bottom surface, an opposite top surface, a side surface and an outer perimeter. The at least one printed circuit board is disposed on the top surface of the cushioning layer. The outer perimeter of the cushioning layer extends two dimensionally in all directions beyond a footprint of each of the at least one printed circuit board. Some of the at least one printed circuit boards have at least one surface mounted electronic component. A polymer layer encloses the top surface of each of the at least one printed circuit boards having the at least one surface mounted electronic component. The polymer layer is in contact with only a portion of the cushioning layer not covered by the at least one circuit board; the polymer layer being disposed inward from the outer perimeter of the cushioning layer. A top coat completely encloses the polymer layer and extends to the outer perimeter of the cushioning layer.

Still another aspect of the present invention is directed to a medical patch having a top surface, an opposite bottom surface and an outer perimeter extending between a trailing end and an opposite leading end. The medical patch includes: a first adhesive centrally disposed inward from the outer perimeter on only a portion of the bottom surface of the medical patch; a second adhesive disposed only proximate its outer perimeter on the bottom surface of the medical patch without overlapping the first adhesive, wherein the second adhesive exhibiting a higher peel force than that of the first adhesive. The medical patch also has a multi-piece liner including: a central liner disposed on only a portion of the bottom surface of the patch completely covering the first adhesive, wherein an outer perimeter of the central liner is disposed inward a predetermined distance from the outer perimeter of the patch; a leading end outer perimeter liner covering only a leading portion of the bottom surface of the medical patch proximate the leading end and extending to the outer perimeter of the medical patch; and a trailing end outer perimeter liner covering only a trailing portion of the bottom surface of the medical patch disposed proximate the trailing end and extends to the outer perimeter of the medical patch. Each of the outer perimeter liners are laterally folded over onto itself with its outer contour substantially aligned. The outer perimeter liners are arranged so that respective folds of each of the outer perimeters abut one another along a fold line interface thereby defining an opening that exposes the first adhesive. The central liner overlaps only a portion of each of the outer perimeter liners, while the outer perimeter liners together with the central liner completely cover the bottom surface of the medical patch.

One other aspect of the present invention is directed to a medical patch having a top surface, an opposite bottom surface and an outer perimeter extending between a trailing end and an opposite leading end. The medical patch includes: a first adhesive centrally disposed inward from the outer perimeter on only a portion of the bottom surface of the medical patch; a second adhesive disposed only proximate its outer perimeter on the bottom surface of the medical patch without overlapping the first adhesive, wherein the second adhesive exhibiting a higher peel force than that of the first adhesive. The medical patch also has a multi-piece liner including: a central liner disposed on only a portion of the bottom surface of the patch completely covering the first adhesive, wherein an outer perimeter of the central liner is disposed inward a predetermined distance from the outer perimeter of the patch; a leading end outer perimeter liner covering only a leading portion of the bottom surface of the medical patch proximate the leading end and extending to the outer perimeter of the medical patch; and a trailing end outer perimeter liner covering only a trailing portion of the bottom surface of the medical patch disposed proximate the trailing end and extends to the outer perimeter of the medical patch. Each of the outer perimeter liners are laterally folded over onto itself with its outer contour substantially aligned. The outer perimeter liners are arranged so that respective folds of each of the outer perimeters abut one another along a fold line interface thereby defining an opening that exposes the first adhesive. The central liner overlaps only a portion of each of the outer perimeter liners, while the outer perimeter liners together with the central liner completely cover the bottom surface of the medical patch. Each of the outer perimeter liners when folded defines two overlapping sections including a contacting section which is in contact with only the second adhesive, and an opposite non-contacting section not in contact with either of the adhesives. A leading end outer perimeter pull tab extends from the non-contacting section of the leading end outer perimeter liner beyond the outer perimeter of the medical patch, while a leading end adherence tab extends from the non-contacting section of the leading end outer perimeter liner into the opening. Similarly, a trailing end outer perimeter pull tab extends from the non-contacting section of the trailing end outer perimeter liner beyond the outer perimeter of the medical patch, while a trailing end adherence tab extends from the non-contacting section of the trailing end outer perimeter liner into the opening.

Another aspect of the present invention is directed to a method for applying to a human body the medical patch as described in the preceding paragraph. First, the central liner is removed thereby exposing the first adhesive, while the outer perimeter liners are maintained in place adhered to the medical patch. With the first adhesive exposed, the medical patch is positioned on the human body and adhered via the first adhesive. Next, with a first hand, pressing down from the top surface the trailing end of the patch while simultaneously, with a second hand, pulling the leading end outer perimeter liner pull tab to remove the leading end outer perimeter liner and expose the second adhesive underneath. Then, with the second hand, pressing down from the top surface the leading end of the patch while simultaneously, with the first hand, pulling the trailing end outer perimeter liner pull tab attached to remove the trailing end outer perimeter liner and expose the second adhesive underneath.

Still yet another aspect of the present invention is directed to a self-positioning neurostimulation medical patch for stimulation of a sacral (S3 foramen) spinal nerve, wherein the medical patch has a top surface, a bottom surface, an outer perimeter, a leading end and an opposite trailing end, the leading and trailing ends defining a central longitudinal axis. An electrode generates an electrical signal, wherein the electrode is disposed proximate the leading end of the medical patch. The bottom surface of the medical patch is covered by a liner. The outer perimeter of the medical patch has a linear section disposed symmetrically on both sides of the central longitudinal axis. These linear sections are oriented at an angle of approximately ±60 degrees relative to the central longitudinal axis while the electrode is disposed at an intersection of parallel lines approximately 2 cm inward relative to the respective linear sections.

While yet another aspect of the present invention relates to a method for unassisted self-positioning of the neurostimulation medical patch as described in the preceding paragraph. Initially, a tail bone is located via tactile manipulation. Then, approximately 9 cm upwards along the spine from the tail bone is measured to identify an anatomical reference point. Lastly, the medical patch is positioned so that an end of one of the linear sections closest to the central longitudinal axis substantially coincides with the anatomical reference point and that linear section is substantially aligned with the spine.

BRIEF DESCRIPTION OF THE DRAWING

The foregoing and other features of the present invention will be more readily apparent from the following detailed description and drawings of illustrative embodiments of the invention wherein like reference numbers refer to similar elements throughout the several views and in which.

DETAILED DESCRIPTION OF THE INVENTION

The present invention is directed to a medical patch to transdermally deliver a treatment therapy to a target site of the body. In accordance with the present invention, the treatment therapy provided by the medical patch to the target site of the body may include electrical stimulation and/or delivery of a pharmacological agent such as pain medication, drugs or hormones. By way of illustrative example, the medical patch is shown and described as providing neurostimulation to one or more targeted nerves via electrical stimulation. It is understood that the present inventive transdermal medical patch may be adapted to provide treatment therapy to any desired target site of the body (not just one or more nerves) and deliver a pharmacological agent in addition to, or instead of electrical stimulation. Both the type of treatment therapy provided and the target site may be selected, as desired, depending on the medical condition being treated.

Figure 1A:
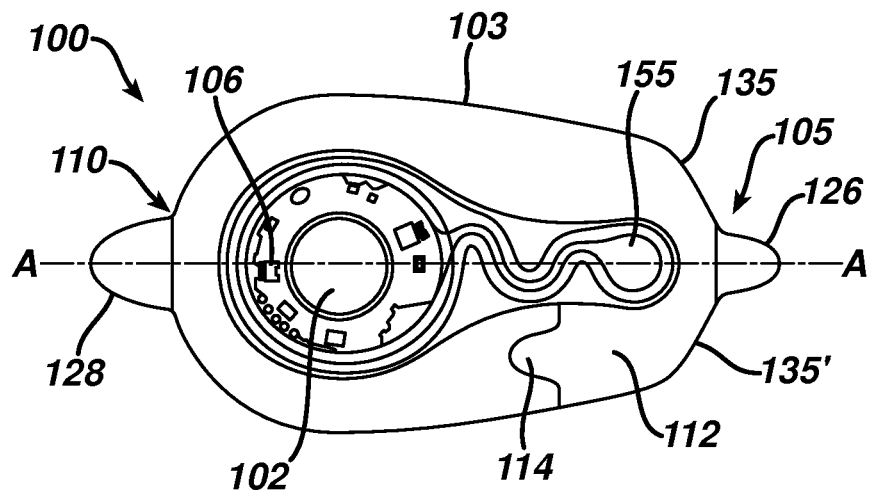
FIG. 1A is a top view of an exemplary neurostimulation medical patch in accordance with the present invention with the top protective covering and multi-piece liner intact.
Figure 1B:
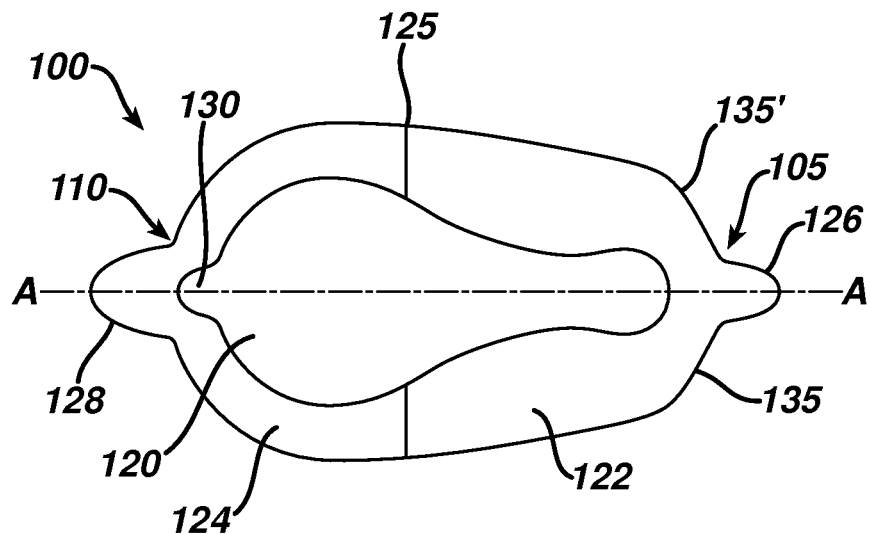
FIG. 1B is a bottom view of the neurostimulation medical patch of FIG. 1A.
Figure 1C:
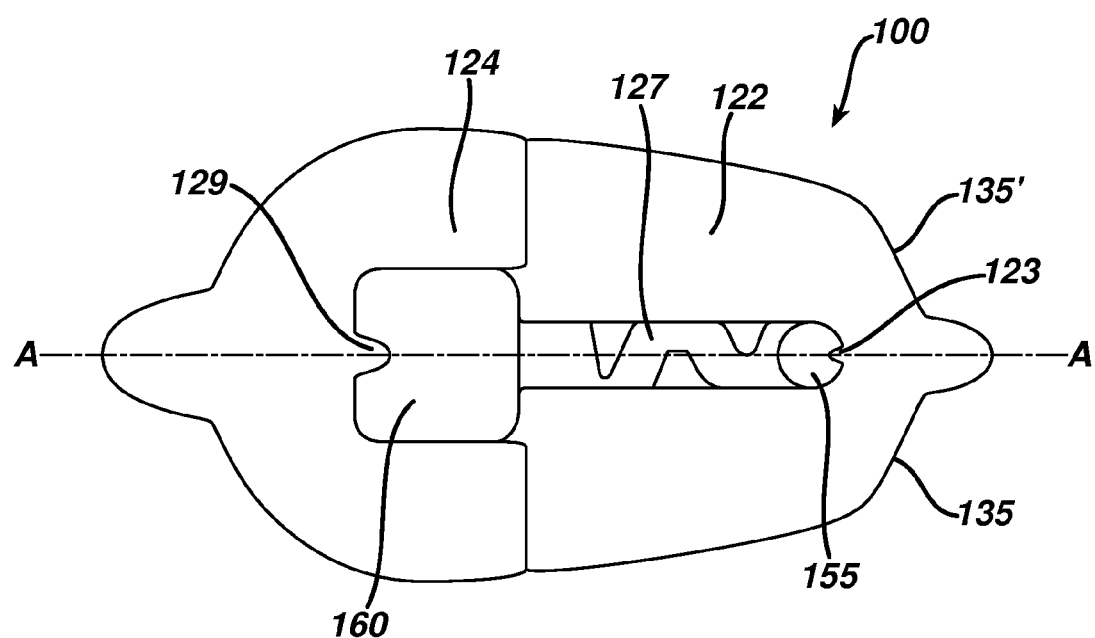
FIG. 1C is a bottom view of the neurostimulation medical patch of FIG. 1A after the central liner has been removed leaving intact both outer perimeter liners.
Figure 1D:
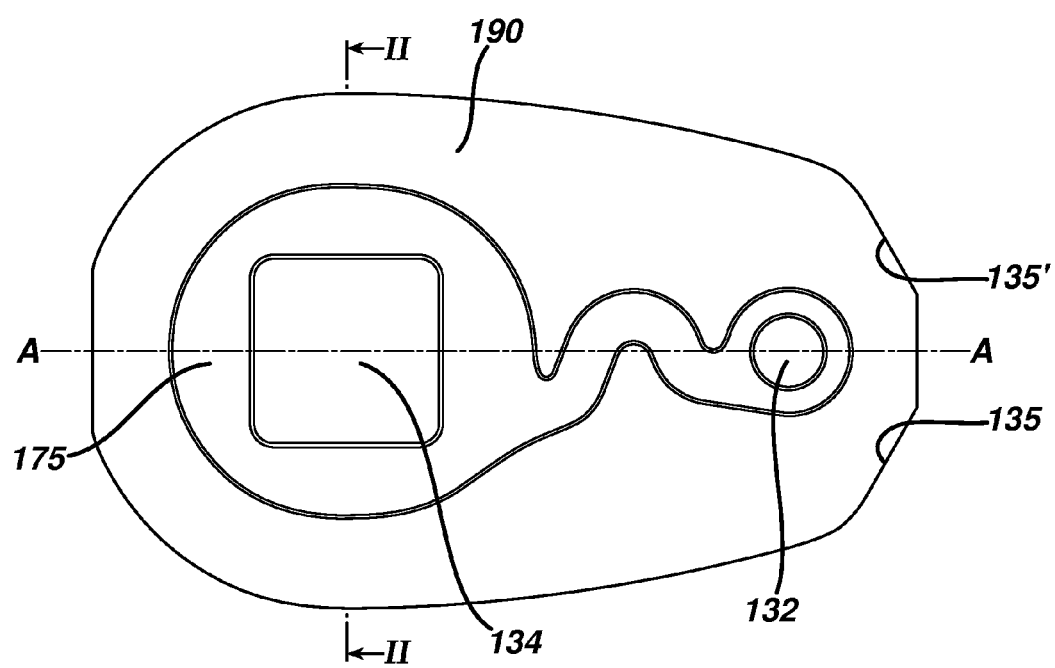
FIG. 1D is a bottom view of the neurostimulation medical patch of FIG. 1A with the central liner and both outer perimeter liners removed.
Figure 1E:
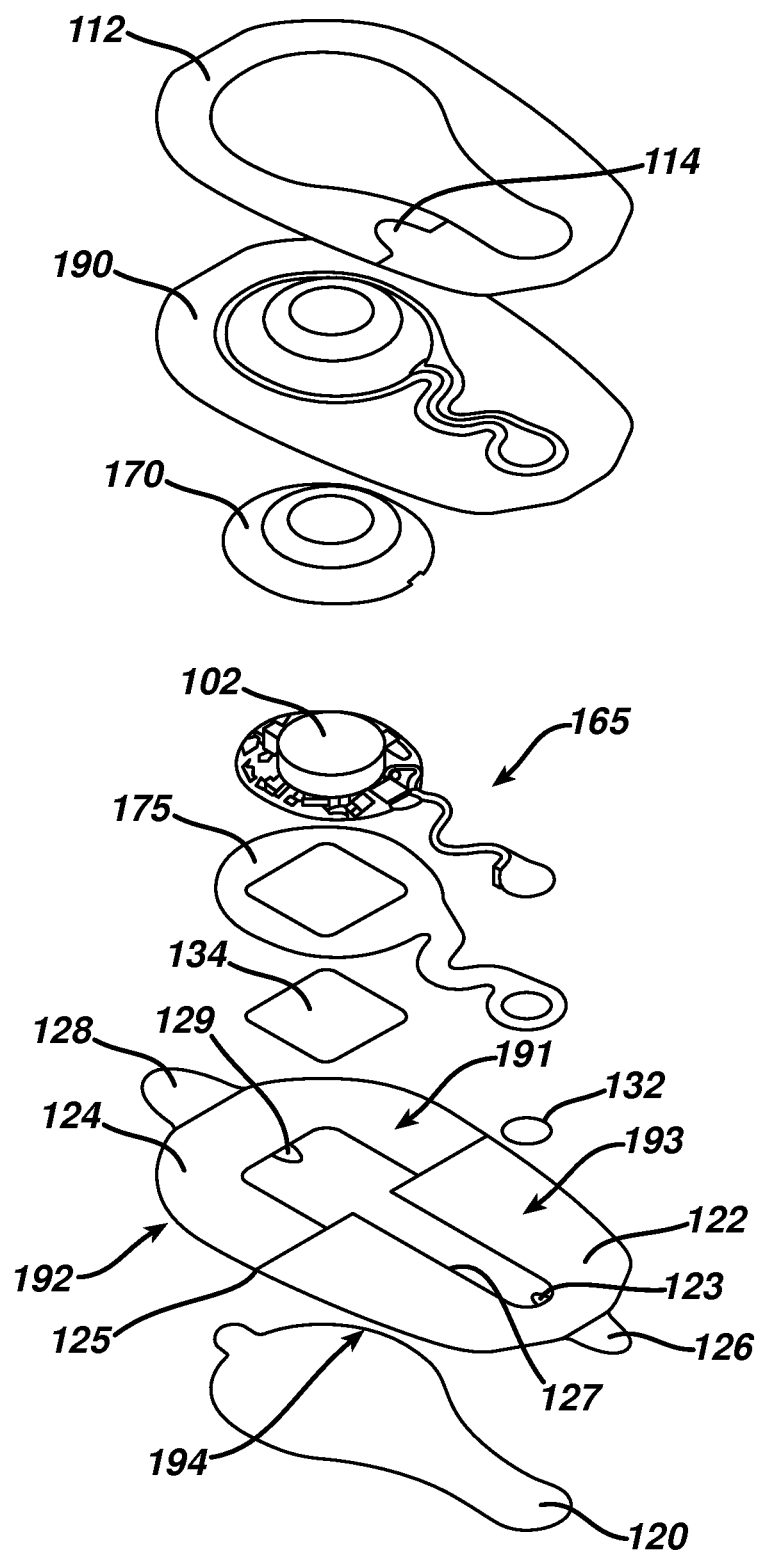
FIG. 1E is an exploded view of the neurostimulation medical patch of FIG. 1A.
Figure 1F:
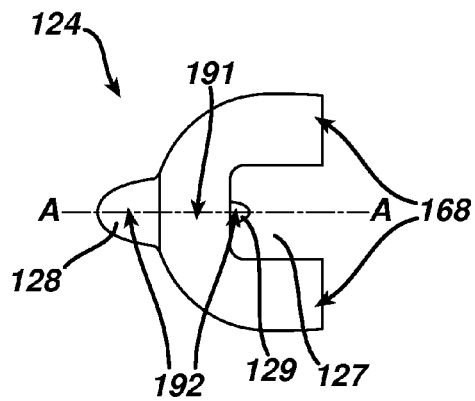
FIG. 1F is a front view of the contacting section of the trailing end outer perimeter liner of FIG. 1C folded onto itself.
Figure 1G:
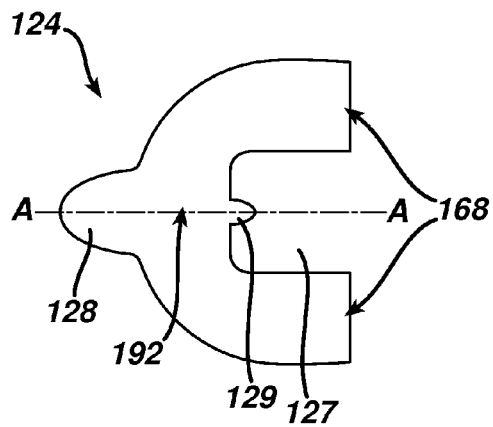
FIG. 1G is a front view of the non-contacting section of the trailing end outer perimeter liner of FIG. 1C folded onto itself.

FIG. 1A is a top view of the exemplary medical patch 100, such as a nerve stimulation patch, with the top protective covering and multi-piece liners intact. An exploded view of the medical patch in FIG. 1A is depicted in FIG. 1E. Patch 100 has an outer perimeter 103 that extends between a leading end 105 and an opposite trailing end 110.

During storage and prior to placement on a patient, the medical patch is protected by a removable top protective covering 112. A pull tab 114 may be grasped and pulled upwards to assist in removal of the top protective covering 112 from a raincoat or top coat 190. The top coat 190, provides a water resistant barrier for the electronics of the medical patch enclosed beneath it. Top coat 190, preferably a clear polyurethane film coated with an acrylic base biocompatible skin adhesive, completely covers and extends beyond the footprint of the electronic circuitry 165 so that a region of the top coat proximate its outer perimeter is secured to the skin via the biocompatible skin adhesive coating disposed on its bottom surface. To maximize the duration in which the top coat 190 remains adhered to the skin, the thickness of the top coat 190 is preferably less than or equal to approximately 0.001 inch.

Preferably, top coat 190 has a relief contour substantially conforming to that of electronic circuitry 165 which includes one or more electrical components powered by a power source 102, for example, a battery. Rather than having an internal battery 102, as shown throughout the figures, an external power source may power the medical patch remotely such as during RF communication. Communication between the medical patch and an external device, for example, a control device or programmer, is provided by transmitter/receiver circuitry 106 (also referred to as optical element or optical eye) included as part of the electronic circuitry in the medical patch. Of course, the electronic circuitry 165 may be modified, as desired, depending on the treatment therapy provided. In the case of a medical patch that provides electrical stimulation, the electronic circuitry further includes one or more electrodes for providing electrical stimulation to a targeted nerve when adhered to the body. Patch 100, in the exemplary configuration depicted throughout the figures, has two electrodes, e.g., a first electrode 155 disposed proximate the leading end 105 (as shown in FIG. 1E) and a second electrode 160 (as seen in FIG. 1C visible below the respective transparent adhesive gel pads) proximate the trailing end 110. Any number of one or more electrodes may be employed, as desired, to provide electrical stimulation. The medical patch may be designed without any electrodes, instead providing only delivery of a pharmacological agent as the prescribed therapy treatment. By way of illustrative example, in the first electrode 155 is circular in shape, while the second electrode 160 is in the shape of a square. The shape and size of each electrode may be modified, as desired, to produce a desired electric field sufficient in strength and shape to stimulate at least one targeted nerve.

Figure 2A:
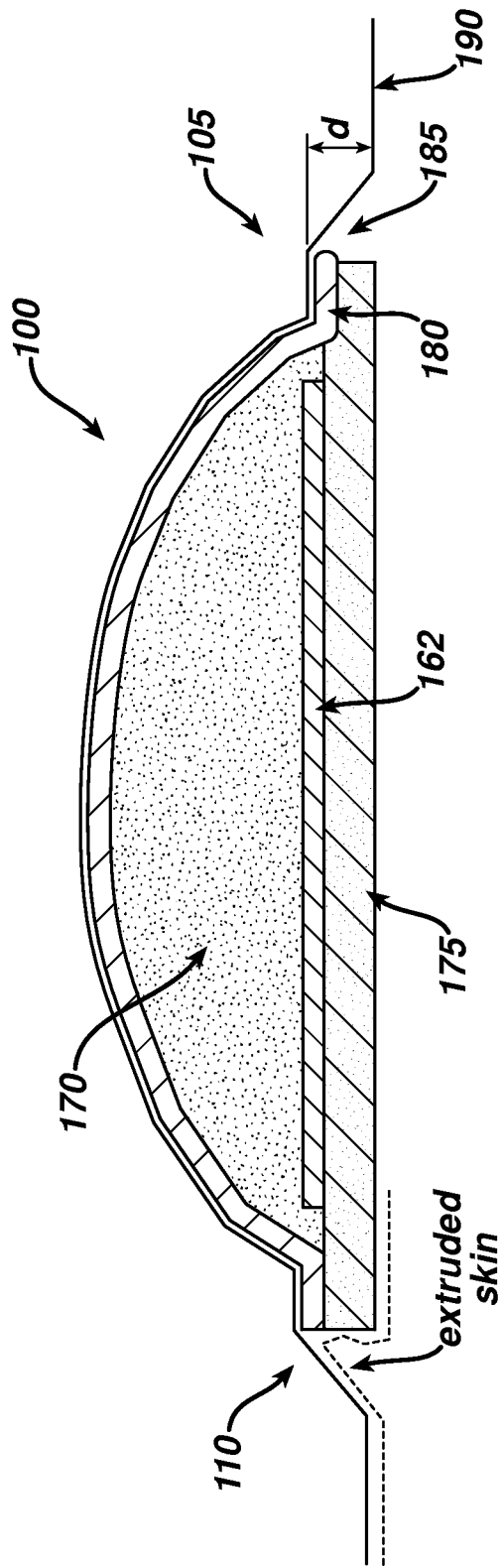
FIG. 2A is a cross-sectional view of the patch in FIG. 1D along line II-II.

Some of the electronic circuitry 165, specifically, the power source and any other surface mounted components secured to a printed circuit board, is bonded and encapsulated by a polymer 170, such as clear, solid Ethylene Vinyl Acetate (EVA) Surebonder 707 sold by FPC Corporation, Wauconda, Ill. Top coat 190 covers polymer 170. The polymer provides enhanced rigidity to the otherwise flimsy patch while hermetically sealing the electronic circuitry from air and moisture. Any biocompatible/non-toxic polymers may be used. Preferably, the polymer is transparent or clear to allow optical bidirectional infrared data communication between the electronic circuitry of the medical patch and an external control device. If desired, a cosmetic cover layer 180 (as shown in FIG. 2A), preferably flesh colored, may be disposed between the polymer 170 and top coat 190 so that the medical patch is less conspicuous.

Electronic circuitry that is rigid and inflexible (e.g., printed circuit boards or any other rigid substrate) when placed in direct contact with the skin may cause irritation. To reduce or minimize skin irritation, a cushioning layer is disposed beneath all printed circuit boards associated with electronic circuitry 165 preventing direct contact with the skin. For the embodiment illustrated in FIG. 1E, electronic circuitry 165 includes rigid printed circuit boards disposed atop the respective square 160 and circular 155 electrodes. Any biocompatible and non-allergenic material that serves as a cushion may be employed as the cushioning layer such as, but not limited to, polyurethane foam preferably having a thickness greater than approximately 0.012 inch, more preferably in the range of approximately 0.014 inch—approximately 0.018 inch, most preferably approximately 0.016 inch. Other desired properties for the cushioning layer material selected includes a relatively high moisture-vapor transition rate (MTVR), preferably greater than approximately 500 $gm/m^2/24$ hour, that wicks moisture away from underneath the patch. To prevent direct contact between the printed circuit board associated with the electronic circuitry 165 and the skin, the footprint or outer perimeter of cushioning layer 175 is greater than/extends beyond that of each of the printed circuit boards, preferably greater than approximately 0.030 inch, more preferably in a range between approximately 0.050 inch to approximately 0.150 inch, depending on the geometry/layering of patch materials that make up the transition between the patch and the skin. To insure covering of the corners as well as accommodate manufacturing tolerances in placement, as a general rule the cushioning layer extends beyond the printed circuit boards by approximately 1.5-2 times the thickness of the cushioning layer. For instance, a preferred cushioning layer thickness is approximately 0.016 inch, so the footprint or outer perimeter of cushioning layer 175 extends beyond that of the printed circuit boards by approximately 0.32 inch. To insure that the electrical signals generated by the electrodes 155, 160 are in direct contact with the skin, a corresponding number of openings similar in size and shape to the respective electrodes are defined in the cushioning layer 175 and substantially aligned therewith.

Pads, components or elements 132, 134 made of an electrolytic adhesive such as Ludlow Hydrogel Material (PR90093) sold by Covideien Medical Supplies, Chicopee, Mass., cover at least a portion of, preferably the entire bottom surface of, each of the electrodes 155, 160. These pads serve a dual function to both assist in the delivery of electrical signals while simultaneously providing a temporary/repositionable adhesive. Accordingly, the peel force of the temporary/repositionable adhesive is sufficiently low that the adhesive may be removed from the skin with negligible, if any, discomfort or skin damage, yet be sufficient to support the weight of the medical patch (e.g., less than approximately 30 grams). Pads 132, 134 are each, preferably, approximately the same size and shape of the associated electrode 155, 160 which it covers. The size and shape among each of the hydrogel pads may either be the same or different. Typically, the hydrogel material used for the pads 132, 134 is the same.

The adhesive coating on the bottom surface of top coat 190 has a higher peel force preferably in the range of approximately 1.26 lb/in-approximately 2.98 lb/in, than that provided by the electrolytic adhesive pads 132, 134. On the one hand, the hydrogel pads 132, 134 provide a temporary, yet repositionable, adherence of the medical patch to the skin. This, as will be explained in greater detail below, allows the same medical patch to be removed from the skin and repositioned when not placed correctly on the body over the target site of interest. On the other hand, the adhesive coating disposed on the bottom surface of the top coat proximate its outer perimeter (where not covered by the cushioning layer) provides a stronger adhesive bond with the skin that maintains the patch in place for an extended period of time, for example, approximately 7 or more days.

Prior to use, the entire bottom surface of the medical patch 100 is covered by a multi-piece liner. FIG. 1B is a bottom view of the medical patch 100 in FIG. 1A. The exemplary multi-piece liner shown and described herein is a three-piece liner including: a central liner 120 completely covering all of the hydrogel pads 132, 134; a leading end outer perimeter liner 122 covering the bottom surface of the patch proximate the outer perimeter of the leading end 105 of the patch, and a trailing end outer perimeter liner 124 covering the bottom surface of the patch proximate the outer perimeter of the trailing end 110 of the patch. Preferably, the central liner 120 is a single continuous sheet. Each of the outer perimeter liners 122, 124 are folded over in a lateral direction perpendicular to a central longitudinal axis A-A substantially in half on to itself along respective fold lines 166, 168 (as shown in FIGS. 1F-1I) with their respective outer contours aligned. That portion or half of the outer perimeter liner in contact with only the adhesive coating on the bottom surface of the top coat 190 proximate its outer perimeter is hereinafter referred to as the "contacting section" (191, 193 in FIGS. 1F-1I), while an opposite folded over exposed portion or half of the outer perimeter liner not in contact with the adhesive coating on the bottom surface of the top coat (or any other adhesive) is referred to as the "non-contacting section" (192, 194 in FIGS. 1F-1I). When adhered to the medical patch, the central liner 120, leading end outer perimeter liner 122 and trailing end outer perimeter liner 124 together completely cover the bottom surface of the patch. Furthermore, the fold line 166 of the leading end outer perimeter liner 122 and the fold line 168 of the trailing end outer perimeter liner 124 abut one another along a fold line interface 125 thereby forming a central opening 127 encompassing the hydrogel pads 132, 134. In one particular embodiment, fold line interface 125 is approximately midway along the central longitudinal axis A-A between the leading and trailing ends 105, 110, respectively, of the medical patch. Central liner 120 has a slightly larger footprint, preferably greater than approximately 0.100 inch, than that of central opening 127 while overlapping with only a portion of each of the perimeter liners 122, 124. A central liner pull tab 130 projects from the either end of the central liner 120 along the central longitudinal axis. When grasped and pulled upwards the pull tab 130 assists in removal of the central liner 120.

Figure 1H:
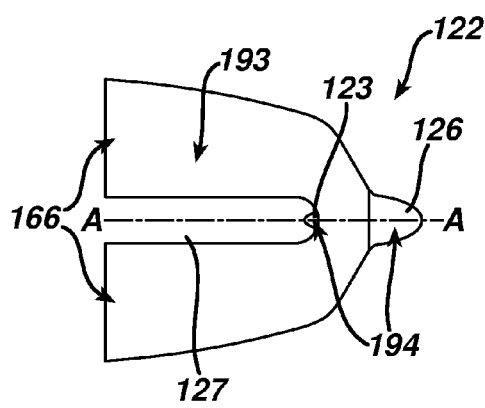
FIG. 1H is a front view of the contacting section of the leading end outer perimeter liner of FIG. 1C folded onto itself.
Figure 1I:
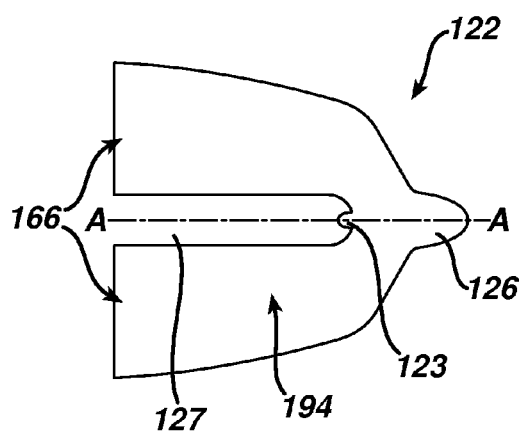
FIG. 1I is a front view of the non-contacting section of the leading end outer perimeter liner of FIG. 1C folded onto itself.

The respective non-contacting section 194, 192 of each of the outer perimeter liners 122, 124 has two associated tabs. Referring to FIGS. 1H & 1I, pull tab 126 projects from the leading end 105 of the leading end outer perimeter liner 122 along the central longitudinal axis A-A, while an adherence tab 123 is similarly disposed along the central longitudinal axis A-A and projects into the central opening 127 overlapping on to hydrogel pad 132. Similarly, a pull tab 128 projects from the trailing end 110 of the trailing end outer perimeter liner 124 along the central longitudinal axis A-A, while an adherence tab 129 is similarly disposed along the central longitudinal axis A-A and projects into the central opening 127 overlapping on to hydrogel pad 134. No tabs are associated with the contacting section 193, 191 of either of the outer perimeter liners 122, 124.

Pull tab 126 associated with the leading end outer perimeter liner 122 may be grasped and pulled from the bottom surface of the patch starting from the fold line interface 125. Thereafter, in a similar manner, the trailing end outer perimeter liner 124 may be removed from the bottom surface of the patch starting from the fold line interface 125 using pull tab 128. As a result of this inventive design, the medical patch remains stable on the skin in the proper location when the adhesive layer disposed on the bottom surface of the patch proximate its outer perimeter is deployed or exposed without pulling off the hydrogel pads that serve as a temporary/repositionable adhesive. Adherence tabs 123, 129 projecting from respective non-contacting sections 194, 192 adhere to hydrogel pads 134, 132, respectively, thereby securing the non-contacting sections of the leading and trailing end outer perimeter liners in place until pull tabs 126, 128 are pulled for liner deployment.

FIG. 1C is a bottom view of the medical patch with the central liner 120 removed; while the leading and trailing end outer perimeter liners 122, 124 remain intact. FIG. 1D is a bottom view of the patch after the removal of the multi-piece liner (e.g., the central liner 120, leading end outer perimeter liner 122 and trailing end outer perimeter liner 124).

During storage, the medical patch is enclosed in a protective pouch, preferably made of a relatively low permeation packaging material/configuration, or a covered tray such as a thermoform plastic blister tray with Tyvek® lid. The medical patch is taken out of the packaging and the central liner 120 is removed from the bottom surface of the medical patch by grasping and pulling tab 130 upwards exposing hydrogel pads 132, 134 underneath. Due to the temporary/repositionable adherence characteristics of the selected hydrogel material, the medical patch temporarily adheres to the surface of the skin via the hydrogel pads 132, 134. However, the tackiness is described as "temporary" since its adhesive properties allow the medical patch to be readily removed from the skin and repositioned, if necessary, for proper orientation over the target site. Once the medical patch has been properly positioned on the body the user presses down on the top of the patch to secure the hydrogel pads to the skin.

Figure 1J:
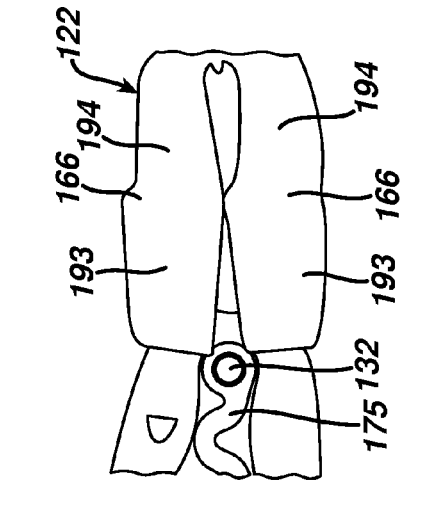
FIGS. 1J-1L illustrate sequential steps in removing the leading end outer perimeter liner from the bottom of the medical patch.
Figure 1K:
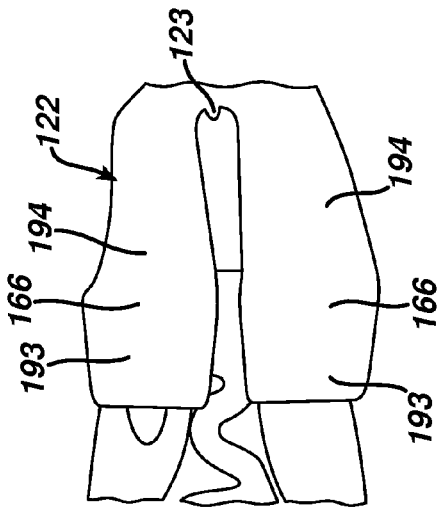
Figure 1L:
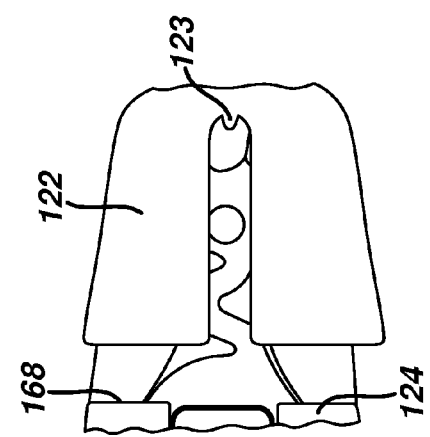
Figure 1M:
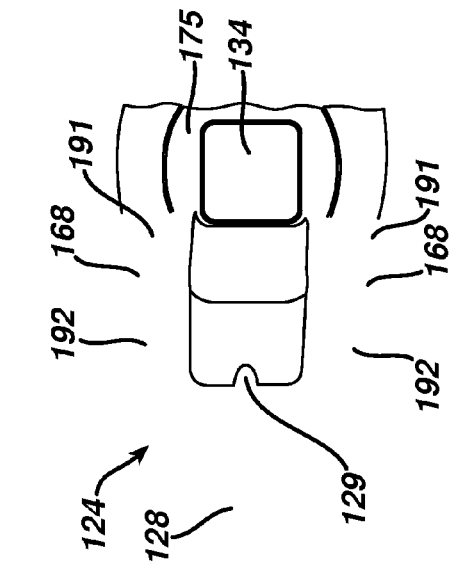
FIGS. 1M & 1N illustrate sequential steps in removing the trailing end outer perimeter liner from the bottom of the medical patch.
Figure 1N:
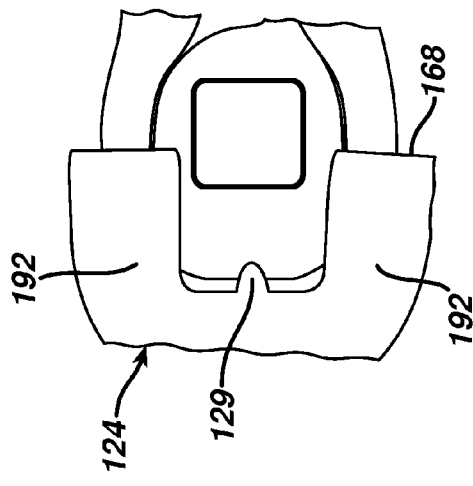

Next, outer perimeter liners 122, 124 are removed one at a time, as sequentially illustrated in FIGS. 1J-1N. With one hand the user holds down the trailing end 110 of the patch while pulling along the skin the leading end pull tab 126 of the patch in a direction opposite the trailing end 110 until the leading end outer perimeter liner 122 is removed from the patch exposing the adhesive coating on the bottom surface of the top coat 190 (FIGS. 1J-1L). After being removed, the user smoothes the exposed adhesive coating against the skin. A similar process is repeated next by switching hands and pressing down to hold the leading end 105 of the patch while pulling along the skin the trailing end pull tab 128 of the patch in a direction opposite the leading end 105 until the trailing end outer perimeter liner 124 is removed from the patch (FIGS. 1M & 1N). Thereafter, the user smoothes the exposed adhesive coating on the bottom surface of the top coat 190 against the skin. A predetermined period of time, preferably approximately 5 minutes, is allowed to pass to insure that the skin properly adheres to the exposed adhesive beneath the outer perimeter liners 122, 124. Upon expiration of the predetermined period of time, the top protective covering 112 is removed by pressing down to hold the patch with one hand while grasping the pull tab 114 with the other hand and pulling in a circular motion. Once again, to insure a proper seal of the top coat 190 with the skin the user presses down along the top surface of the patch.

FIG. 2A is a cross-sectional view of the medical patch in FIG. 1D along line II-II. The power source 102 and any other surface mounted electronic components that are secured to the printed circuit board are generically represented as a block hereinafter referred to as an electronic unit for the medical patch and denoted by reference element 162. In the drawings, electronic unit 162 is generically represented as a block, however, its side profile or contour may vary depending on the circuitry employed. Electronic unit 162 is enclosed or sealed along its top surface and sides by the polymer 170. Top coat 190, preferably completely covers the top surface of the polymer 170. If desired, a cosmetic cover layer 180, preferably flesh colored, may be disposed between the polymer 170 and top coat 190 so that the medical patch is less conspicuous.

Referring to FIG. 2A, top coat 190 tents or slopes away from the outer perimeter of the patch before contacting the skin thereby resulting in a void or gap 185 (substantially triangular in shape) into which the skin extrudes or pushes. A vertical transition or step "d" represents the distance from where the top coat no longer contacts the patch to where it contacts the skin. If the vertical transition or step "d" within the void or gap 185 is too large, excessive extrusion of the skin into the void will result in skin irritation. It is therefore desirable to limit the vertical transition or step "d" of the void or gap 185 to preferably less than approximately 0.018 inch, most preferably less than or equal to approximately 0.016 inch, thereby minimizing the amount of skin that extrudes or pushes into the void 185.

Figure 2B:
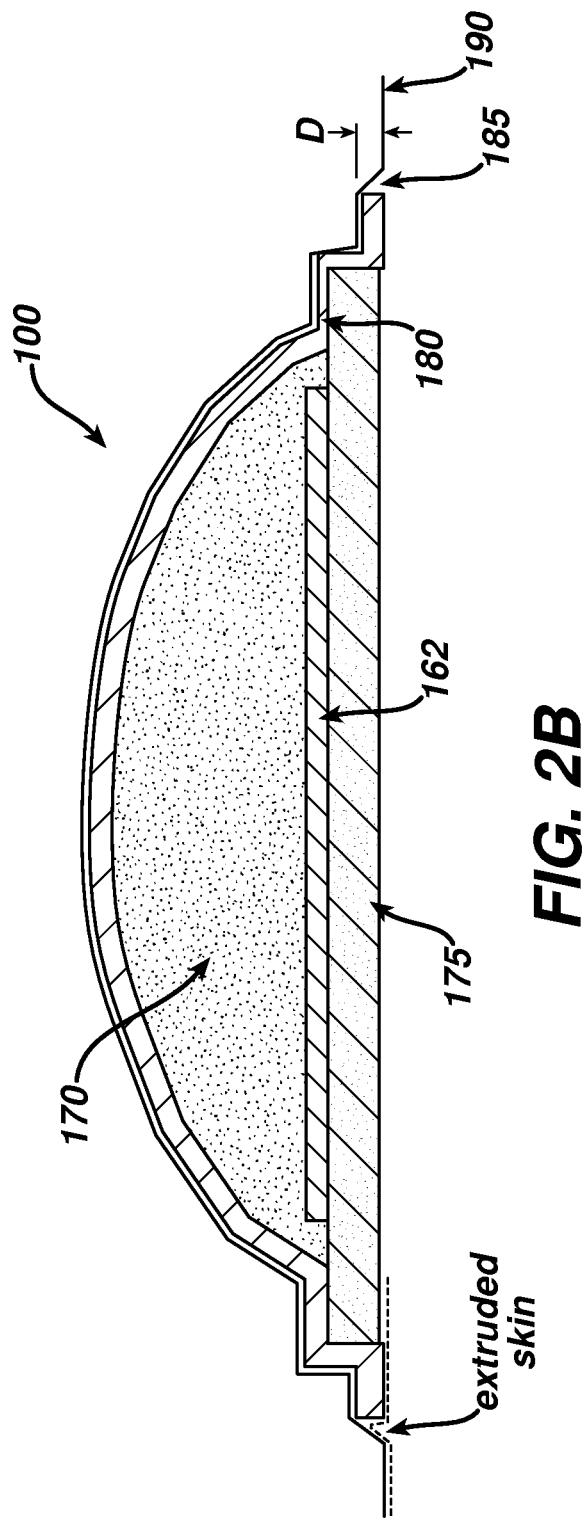
FIG. 2B is a cross-sectional view of an alternative embodiment of the patch in FIG. 1D along line II-II with a compensated step-down transition of the cosmetic cover and top coat to minimize skin extrusion.
Figure 2C:
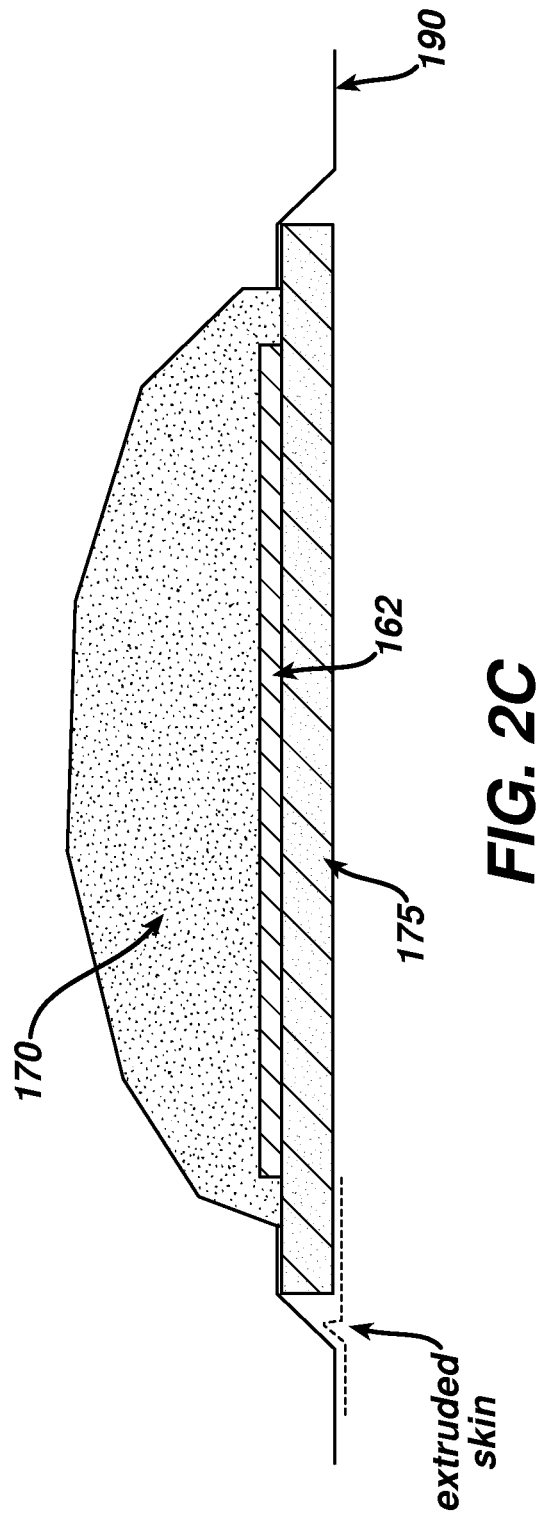
FIG. 2C is a cross-section view of yet another embodiment of the patch in FIG. 1D along line II-II in which the cosmetic cover has been eliminated and the cushioning layer is configured to minimize skin extrusion.

To achieve this desired result, cosmetic cover 180 may be extended so that it steps-down, transitions, or conforms to the side of the cushioning layer 175 and outward from the patch, as illustrated in FIG. 2B. The vertical transition or step "D" is now within an acceptable range less than approximately 0.018 inch. In an alternative embodiment, the cosmetic covering 180 may be eliminated altogether, whereby to avoid skin extrusion into the void the thickness of the cushioning layer itself is approximately 0.014 inch-approximately 0.018 inch, most preferably approximately 0.016 inch. Top coat 190 may be manufactured to conform in physical contact with at least a portion of the sides of the cushioning layer 175 so that the vertical transition or step from where the top coat no longer contacts the cushioning layer to the skin is less than approximately 0.018 inch, as illustrated in FIG. 2C.

Figure 3:
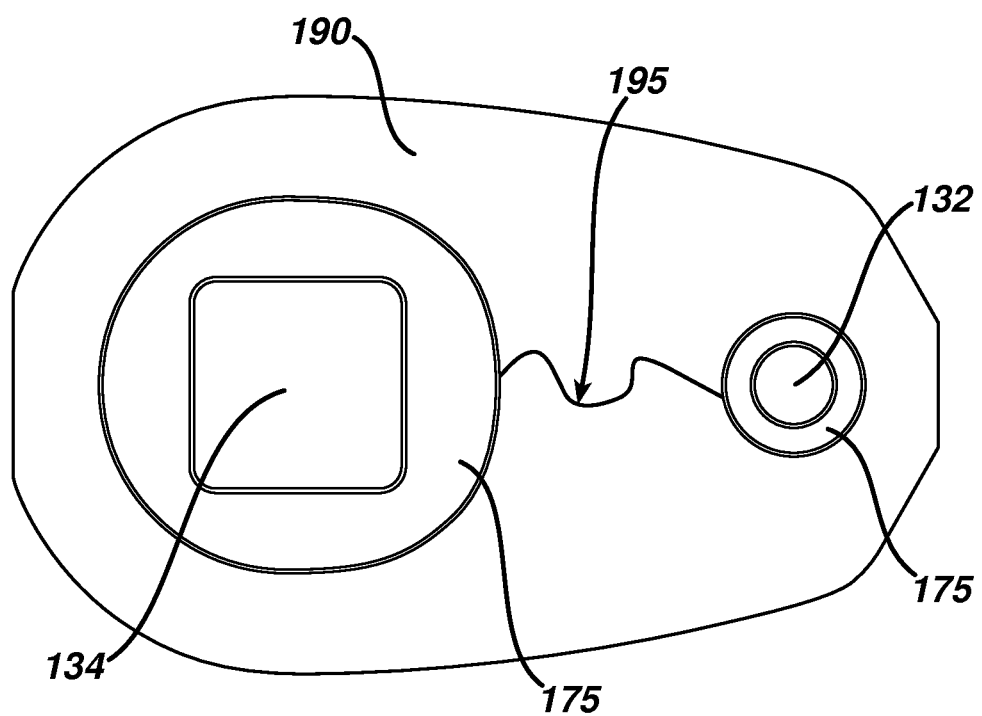
FIG. 3 is a bottom view of still another configuration of the patch in accordance with the present invention in which the serpentine path between the electrodes as shown in FIG. 1D is replaced by a relatively thin wire with the cushioning layer removed along the wire between the electrodes.

In FIG. 3, the serpentine path between the electrodes 155, 160 illustrated in FIG. 1D has been replaced by a current carrying electrical wire 195. With this alternative configuration, the cushioning layer 175 aside from being present beneath the electrodes 155, 160 themselves is also not present between the two electrodes along the wire. The reason the cushioning layer may be eliminated between the two electrodes in this embodiment is because the wire is sufficiently flexible and sufficiently soft so as not to irritate the skin when resting on it. Otherwise, a mere layer of clear urethane covering the wire to prevent direct contact with the skin will be sufficient to prevent any skin irritation.

The cushioning layer 175, in the embodiment depicted in FIG. 1D, is a single continuous layer extending beyond a footprint encompassing the printed circuit boards disposed above the respective electrodes 155, 160 and having a corresponding number of discrete openings defined therein complementary in size and shape to be aligned with each of the respective hydrogel pads 132, 134. Whereas, the cushioning layer 175 in FIG. 3 represents one or more discrete sections. Each section of the cushioning layer 175 is associated with and extends beyond a footprint of an associated printed circuit board disposed above the respective electrode 115, 160. An opening is defined in each discrete section of the cushioning layer corresponding substantially in size and shape with the associated hydrogel pad it surrounds. Because there is no adhesive on the bottom surface of the cushioning layer in contact with the skin the electrolytic adhesive material forming the hydrogel pads are prone to "squirt" loose along the opening in the cushioning layer between foam and skin itself. This is particularly problematic with respect to the circular hydrogel element 132 due to its relatively small size having a diameter, preferably approximately 0.369"-approximately 0.419", most preferably approximately 0.394". The exposed adhesive material of the top coat 190 surrounding the electrodes in accordance with the embodiment in FIG. 3 increases the stability of the hydrogel. As a result of the increased stability of the hydrogel the patch adheres to the skin for a longer period of time. Experimental results have substantiated that the configuration in FIG. 3 approximately doubles the number of days in succession that the patch may be adhered to the skin at the same location on the body from approximately 7 days to approximately 14 days. Thus, the cushioning layer preferably surrounds all sides of each electrode to reduce or prevent leaching of the hydrogel material as well as reduce or prevent saltwater bridging/short circuiting of energy between the electrodes.

Figure 4:
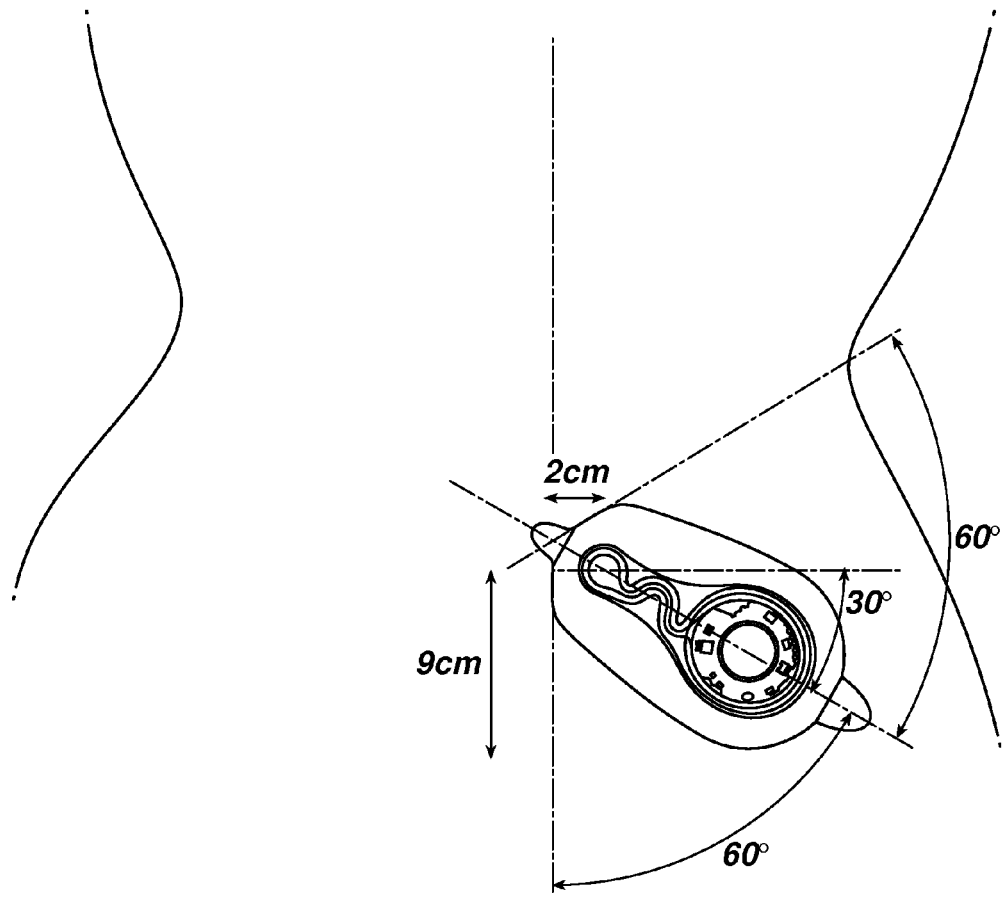
FIG. 4 represents the medical patch of FIG. 1A properly positioned over the sacral (S3 foramen) spinal nerve using the anatomical references without the need for a separate mechanical placement tool.

The neurostimulation medical patch described herein may be properly positioned on the lower back of the body for sacral (S3 foramen) spinal nerve stimulation using tactile and visual senses without the need for a separate mechanical placement tool. Referring to FIG. 4, two anatomical references are useful in locating this underlying nerve bundle. First, the location of the S3 foramen may be approximated by finding the sacrococcygeal junction or tailbone and measuring approximately 9 cm upwards along the spine and approximately 2 cm to either the left or right sides of the body. The sacrococcygeal junction or tailbone may be located by tactile manipulation to find a knuckle-type protuberance at the apex of the sacrum. Second, the sacral (S3 foramen) spinal nerve bundle is disposed along a trajectory of minus approximately 30 degrees relative to a horizontal axis perpendicular to a vertical axis defined by the spine. Based on these two anatomical references, in one particular embodiment, the present inventive medical patch is specifically designed to be properly positioned on the body to provide sacral (S3 foramen) spinal nerve stimulation without the need for a separate mechanical placement device and unassisted.

Specifically, the contour of the outer perimeter of the medical patch and placement of the electrodes are designed for proper positioning on the body without the use of a separate mechanical placement tool. Referring once again to FIG. 1A, medical patch 100 is symmetric about the central longitudinal axis A-A so that the same medical patch may universally be used on either the right or left side of the body. The outer perimeter 103 of medical patch 100 has two linear sections 135, 135' extending from both sides of the leading end pull tab 126. Linear sections 135, 135' are symmetric about the central longitudinal axis A-A of the patch. To avoid any confusion by the user, linear sections 135, 135' are preferably the only linear portions along the outer perimeter of the patch. The center of the leading end electrode 155 is disposed along the central longitudinal axis at the intersection of parallel lines approximately 2 cm inward from the respective linear sections 135, 135' to insure placement of the electrode 155 over the S3 foramen. All other electrodes are substantially aligned along the central longitudinal axis A-A of the medical patch. In addition, linear sections 135, 135' are arranged at an angle off approximately 60 degrees, respectively, relative to the central longitudinal axis of the patch to insure stimulation by the electrodes of the targeted nerve bundle anatomically disposed at a trajectory of minus approximately 30 degrees from a horizontal axis relative to a vertical axis defined by the spine. Constructing the medical patch in accordance with these specific design criteria insures proper placement of the patch and stimulation of the sacral (S3 foramen) spinal nerve bundle without the need for a separate mechanical placement tool.

A brief summary of the methodology is provided for properly positioning the patch on the body to stimulate the sacral (S3 foramen) spinal nerve without the need for a separate mechanical placement tool. Initially, the medical patch is removed from its packaging and placed on a surface with the top side down. The central liner 120 is removed by grasping and pulling the central liner pull tab 130 thereby exposing the hydrogel pads 132, 134 below. Using one hand an index finger is placed on the tailbone. From this anatomical reference point a vertical distance of approximately 9 cm upwards along the spine may be estimated by using the width of either 3 or 4 fingers depending on the size of the individual. For most average size individuals, 9 cm is estimated by the width of four fingers (e.g., index finger, middle finger, ring finger and pinky finger) on one hand outstretched and contacting one another. For larger individuals, 9 cm may be estimated by the width of three fingers (e.g., index finger, middle finger and pinky finger) on one hand held outstretched and contacting one another. While maintaining the pinky finger on the anatomical reference point, using the other hand the medical patch is positioned over either the left or right hand side of the body while satisfying the following criteria: (i) the patch is oriented with the leading end pull tab 126 pointing upwards toward the head; (ii) the intersection of the linear section 135, 135' with the leading end pull tab 126 is substantially aligned with the anatomical reference point; and (iii) the linear section 135, 135' below the leading end pull tab 126 is substantially aligned with the spine. After the medical patch has been properly aligned, the exposed hydrogel pads 132, 134 are pressed down on the skin to form a temporary bond. At this time, if the medical patch needs to be repositioned, the temporary bond between the hydrogel pads and the skin may be disrupted and the medical patch secured once again in place at the correct position. Once the medical patch is temporarily adhered to the body via the hydrogel pads at the correct position to stimulate the target site, the user removes the outer perimeter liners 122, 124 one at a time, starting with the leading end outer perimeter liner. With one hand the user holds down the trailing end 110 of the patch while pulling along the skin the leading end tab 126 of the patch in a direction opposite the trailing end 110 until the leading end outer perimeter liner 122 is removed from the patch. After being removed, the user smoothes the exposed adhesive on the bottom surface of the top coat 190 against the skin. A similar process is repeated next by switching hands and pressing down to hold the leading end 105 of the patch while pulling along the skin the trailing end tab 128 of the patch in a direction opposite the leading end 105 until the trailing end outer perimeter liner 124 is removed from the patch. Thereafter, the user smoothes the exposed adhesive coating on the bottom surface of the top coat 190 against the skin. A predetermined period of time, preferably approximately 5 minutes, is allowed to pass to insure that the skin properly adheres to the exposed adhesive beneath the outer perimeter liners 122, 124. Upon expiration of the predetermined period of time, the top protective covering 112 is removed by pressing down to hold the patch with one hand while grasping the pull tab 114 with the other hand and pulling in a circular motion. Once again, to insure a proper seal of the exposed adhesive of the top coat layer 190 with the skin the user presses down along the top surface of the patch.

Figure 5:
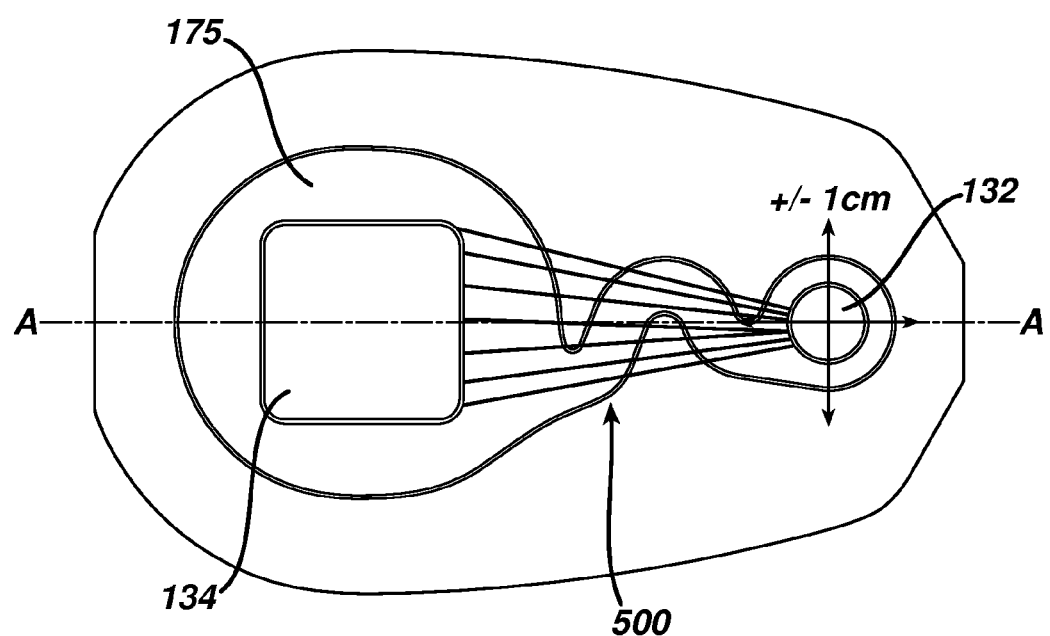
FIG. 5 depicts illustrates the angular and translational forgiveness provided by the circular and square shape electrode configuration of the medical patch in accordance with FIG. 1D.

Self-positioning of the medical patch in accordance with the present invention will rarely be 100% accurately over the sacral (S3 foramen) spinal nerve. Variability that may contribute to placement errors include: (i) variability in patch materials; (ii) placement tool variability (if a placement tool is used); and/or (iii) user error. When positioned 100% accurately, ideally the medical patch is placed so that the leading end electrode 155 substantially coincides with the center of the S3 foramen and the nerve itself resides substantially aligned with the center longitudinal axis A-A approximately 4 cm beneath the skin. The design of the electrodes, i.e., the leading end electrode 155 being circular in shape while the trailing end electrode 160 is square in shape, in combination with the electrodes 155, 160 being disposed substantially aligned with the center longitudinal axis A-A allows for approximately ±1 cm translational tolerance or forgiveness for location of the circular electrode 155 relative to the S3 foramen and approximately ±25° angular tolerance or forgiveness of the center longitudinal axis A-A relative to the nerve itself. In accordance with this inventive medical patch configuration, the electric field lines 500 produced between the circular and square electrodes disposed beneath the respective pads 132, 134 provide this advantageous angular and translational forgiveness, as depicted in FIG. 5.

The present inventive medical patch has been shown and described as providing electrical stimulation to the targeted nerve. It is well understood that stimulation of the target site (e.g., one or more target nerves) may be via electrical stimulation and/or delivery of a pharmacological. Thus, the present inventive features are not limited or restricted to use with medical patches that provide electrical stimulation, nor is the target site limited to just nerves.

Thus, while there have been shown, described, and pointed out fundamental novel features of the invention as applied to a preferred embodiment thereof, it will be understood that various omissions, substitutions, and changes in the form and details of the devices illustrated, and in their operation, may be made by those skilled in the art without departing from the spirit and scope of the invention. For example, it is expressly intended that all combinations of those elements and/or steps that perform substantially the same function, in substantially the same way, to achieve the same results be within the scope of the invention. Substitutions of elements from one described embodiment to another are also fully intended and contemplated. It is also to be understood that the drawings are not necessarily drawn to scale, but that they are merely conceptual in nature. It is the intention, therefore, to be limited only as indicated by the scope of the claims appended hereto.

Every issued patent, pending patent application, publication, journal article, book or any other reference cited herein is each incorporated by reference in their entirety.

What is claimed is:

1. A medical patch having an outer perimeter extending between a leading end and a trailing end, the medical patch comprising:

electronic circuitry including at least one primed circuit board; and a cushioning layer having a bottom surface, an opposite top surface, a side surface and an outer perimeter; the at least one printed circuit board is disposed on the top surface of the cushioning layer; the outer perimeter of the cushioning layer extending two dimensionally in all directions beyond a footprint of each of the at least one printed circuit hoard, wherein some of the at least one printed circuit boards has at least one surface mounted electronic component secured thereto; a polymer layer bonded to and enclosing the top surface of each of the at least one printed circuit board having the at least one surface mounted electronic component; and the polymer layer is in contact with only a portion of the cushioning layer not covered by the at least one printed circuit board; the polymer layer being, disposed inward from the outer perimeter of the cushioning layer; the polymer layer enhancing rigidity of the medical patch while hermetically sealing the electronic circuitry from air and moisture; and a top coat completely enclosing the polymer layer and extending to the outer perimeter of the cushioning layer; the top coat providing a water resistant barrier for the electronic circuitry and the polymer layer disposed beneath the top coat.

2. The medical patch in accordance with claim 1, wherein the cushioning layer is made from a material that wicks moisture away from underneath the patch having a moisture-vapor transition rate (MTVR) greater than approximately 500 $gm/m^2/24$ hour.

3. The medical patch in accordance with claim 2, wherein the cushioning layer is a foam material.

4. The medical patch in accordance with claim 1, wherein the cushioning layer has a thickness in a range between approximately 0.014 inch-approximately 0.018 inch.

5. The medical patch in accordance with claim 1, wherein the electronic circuitry includes more than one electrode and the cushioning layer is a single continuous layer with openings defined therein that encompasses each of the electrodes.

6. The medical patch in accordance with claim 1, wherein a vertical transition distance from where the top coat no longer is in contact with the medical patch to where the top coat is substantially flush with the bottom surface of the cushioning layer is less than approximately 0.018 inch.

7. The medical patch in accordance with claim 6, wherein the vertical transition distance is approximately 0.016 inch.

* * * * *